United States Patent [19]

Garth et al.

[11] Patent Number: 5,360,393
[45] Date of Patent: Nov. 1, 1994

[54] DUAL ADHESIVE STRAP FOR HEAD IMMOBILIZATION

[75] Inventors: Geoffrey C. Garth; James R. Traut, both of Long Beach, Calif.

[73] Assignee: California Medical Products, Inc., Long Beach, Calif.

[21] Appl. No.: 962,389

[22] Filed: Oct. 19, 1992

[51] Int. Cl.$^5$ .............................................. A61F 5/00
[52] U.S. Cl. ..................................... 602/17; 128/870; 602/54; 602/74
[58] Field of Search ................. 128/870, 877; 602/41, 602/42, 54, 57, 74, 58, 59, 78, 17; 604/180

[56] References Cited

U.S. PATENT DOCUMENTS

| | | | |
|---|---|---|---|
| 2,054,768 | 9/1936 | Gale, Jr. | 602/59 |
| 2,337,011 | 12/1943 | Young | 602/58 X |
| 3,469,268 | 9/1969 | Phillips | 602/19 |
| 4,122,857 | 10/1978 | Haerr | 604/180 |
| 4,182,322 | 1/1980 | Miller | 602/17 X |
| 4,299,209 | 11/1981 | Behrens et al. | 602/19 |
| 4,334,530 | 6/1982 | Hassell | 602/57 X |
| 4,339,151 | 7/1982 | Riggs | 128/857 X |
| 4,457,754 | 7/1984 | Buttaravoli | 128/877 X |
| 4,513,739 | 4/1985 | Johns | 602/57 X |
| 4,815,457 | 3/1989 | Mazars et al. | 602/57 |
| 4,884,563 | 12/1989 | Sessions | 602/57 |
| 4,905,712 | 3/1990 | Bowlin et al. | 128/870 |
| 4,928,712 | 5/1990 | Mele | 128/877 |
| 5,098,399 | 3/1992 | Tollini | 128/877 |
| 5,125,907 | 6/1992 | Philpott | 604/180 |
| 5,153,040 | 10/1992 | Faasse, Jr. | 602/57 |

Primary Examiner—Richard J. Apley
Assistant Examiner—Linda C. M. Dvorak
Attorney, Agent, or Firm—Kenyon & Kenyon

[57] ABSTRACT

For securing a patient's head in a head immobilizer, a dual adhesive strap is provided which is designed to lay across and adhere to the patient's forehead and have each of its ends adhere to a spine board. The strap has a bottom side comprising a central region which comprises skin contact adhesive flanked by two regions which comprise board contact adhesive. The board contact adhesive is stronger than the skin contact adhesive, such that the strap stays adhered under various environmental conditions, and the skin of the patient's forehead is not injured by the skin contact adhesive. The strap and the adhesive regions are preferably large enough to accommodate many sizes of heads, spine boards, and head immobilizers. Preferably, a removable backing covers the adhesive side of the strap.

6 Claims, 2 Drawing Sheets

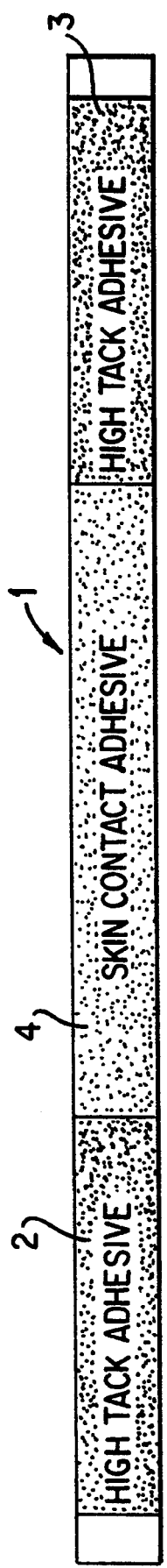
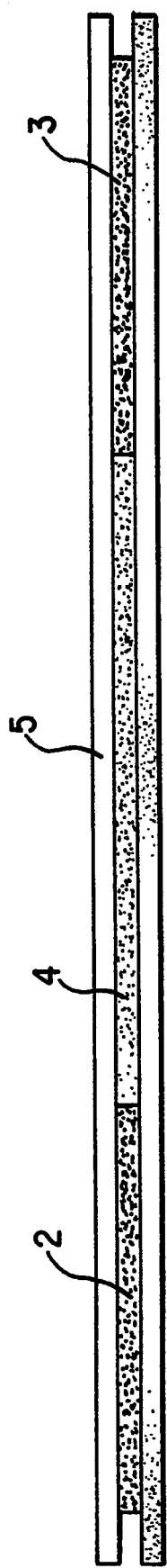
FIG. 1
FIG. 3
FIG. 2

DUAL ADHESIVE STRAP FOR HEAD IMMOBILIZATION

BACKGROUND OF THE INVENTION

The present invention relates to a new and improved adhesive strap for use with devices designed to immobilize a patient's head during emergency medical treatment and transportation.

One of the more common injuries faced by emergency medical personnel is an injury to the neck of a patient. Such injuries present the possibility of damage to the cervical spine from the injury and the possibility of worsening any such damage during treatment and transportation. Due to the severe impairment of function which may result from cervical spine injuries, much care must be taken to immobilize this region during treatment and transportation.

Patients with cervical spine injuries or suspected cervical spine injuries are conventionally placed in a cervical extrication collar, such as those shown in U.S. Pat. No. Re. 32,219, which restricts the patient's head from motion out of the vertical, erect position, and thus, presumably, limits motion of the spine as well. However, such collars often do not sufficiently restrict movement of the head. Therefore, additional, often jury-rigged measures are used to restrict such movement.

Emergency medical personnel often surround a patient's head and body with sandbags or styrofoam blocks. These devices are usually held in place with athletic tape or other strapping means including other adhesive tapes which are cut to size on site and adhered across the patient's body.

Several devices have been developed to immobilize the head more effectively and more efficiently than this jury-rigging. These include the head immobilizers shown in U.S. Pat. Nos. 3,987,777, 4,589,407, 4,594,995, and 4,718,412, and those sold commercially such as the HeadBed ™ and HeadBedII ™ immobilization devices (California Medical Products, Long Beach, Calif.). These devices may obviate the need for such sand-bag or styrofoam block jury-rigging but often still necessitate the use of adhesive strapping means, such as first aid or other tape, to immobilize the patient's head.

Such adhesive strapping means are often not sticky enough to stay adhered to the spine board (or other surface upon which the patient is placed) in the different environmental conditions where it is used (e.g. different conditions of temperature, moisture, or cleanliness of the spine board). Changes in these conditions can lead particularly to insufficient adhesion of the adhesive strap to the spine board or other surface upon which the patient is placed, resulting in inadequate immobilization or complete release of the strap from the spine board. As a result, these strapping means may not efficiently and effectively immobilize the patient's head. Conversely, some adhesive strapping means used to immobilize a patient's head in a head immobilizer are too sticky and cause irritation and injury to the patient's forehead, especially upon removal.

It would, therefore, be desirable to provide an adhesive strap for immobilizing a patient's head that provides improved adhesion to a spine board or other surface under adverse conditions, while reducing or minimizing irritation of the patient's skin as a result of contact with the adhesive strap.

SUMMARY OF THE INVENTION

The dual adhesive strap of the present invention overcomes these problems with adhesive straps used to immobilize a patient's head, providing an efficient and effective means for ensuring that a patient's head stays immobilized during treatment and transport.

In accordance with the present invention, an adhesive strap is provided which comprises a strap substrate and at least two adhesives, or two different concentrations of the same adhesive, on one surface of the strap. The strap substrate is preferably a high tensile polyester fabric, but may be comprised of any similar web material which is resistant to tearing in use. Materials presently used to form other such adhesive straps, tapes or taping strips are also suitable. The adhesive side of the strap comprises two spine board contact adhesive regions flanking an intervening skin contact adhesive region. The board contact adhesive is an adhesive which will better adhere (relative to the adhesive in the skin contact region) to a spine board or other surface upon which the patient is placed in adverse environmental conditions and which resists detachment from the spine board by the forces normally exerted upon the patient's head and cervical spine during transport and treatment. In one preferred embodiment, Ecomelt MI-US1000, Turquoise, commercially available from the Ecomelt Adhesives Division of LEXEM Consolidated of Rock Hill, Conn., is used as the board contact adhesive. Although in this preferred embodiment the spine board adhesive is colored turquoise to visually distinguish the adhesive regions, uncolored adhesives can also be used. However, any adhesive possessing similar adhesive properties relative to the skin contact adhesive may be used. Mixtures of adhesives can also be used.

The skin contact adhesive of the present invention is less strong than the board contact adhesive such that it does not significantly damage or irritate the skin of the patient's forehead, yet is strong enough to resist detachment as a result of the forces normally exerted upon the patient's head and cervical spine during transport. In one preferred embodiment, Ecomelt M300, White, commercially available from the Ecomelt Adhesives Division of LEXEM Consolidated of Rock Hill, Conn., is used as the skin contact adhesive, but other adhesives with similar adhesive properties may be used. Suitable materials include those used in prior adhesive straps, tapes (including without limitation the type of adhesive used on Johnson & Johnson ZONAS ™ tape) and taping materials. Colored adhesives can also be used for the skin contact region. Mixtures of these materials can also be used.

The board contact adhesive regions and the skin contact adhesive region can be of sizes able to accommodate various spine board, head immobilizer, and head sizes. The strap may also have gaps between the adhesive regions which contain no adhesive or another different adhesive. The strap may also have more than one skin contact adhesive region and more than two board contact adhesive regions.

In a preferred embodiment of the present invention, the dual adhesive strap is precut and has a removable backing covering the adhesive side of the strap. This arrangement obviates the need for emergency medical personnel to measure and cut lengths of adhesive strap and also ensures the viability of the adhesives. The adhesive strap may also be provided with adhesive-free tabs at one or both ends to facilitate application and removal of the bandage. In alternative embodiments, the dual adhesive strap of the present invention can be made on rolls from which three-region strips can be torn.

The dual adhesive strap of the present invention may also have indications of the locations of the board contact adhesive regions and the skin contact adhesive region of the strap in the form of colors, wording, or symbols on either side of the strap, preferably on the non-adhesive side of the strap. The center of the strap may also be indicated in this way.

Although the dual adhesive strap of the present invention is designed to be used in conjunction with a head immobilizer, such as for example those sold under the trademarks HeadBed TM and HeadBedII TM by California Medical Products, Long Beach, Calif., it may also be used in conjunction with the sand-bag or styrofoam block jury-rigging referred to above or other head immobilization apparatus.

BRIEF DESCRIPTION OF THE FIGURES

FIG. 1 is a bottom view of an adhesive strap of the present invention.

FIG. 2 is a top view of an adhesive strap of the present invention.

FIG. 3 is a side view of an adhesive strap of the present invention.

DETAILED DESCRIPTION OF PREFERRED EMBODIMENT

Figure 4:
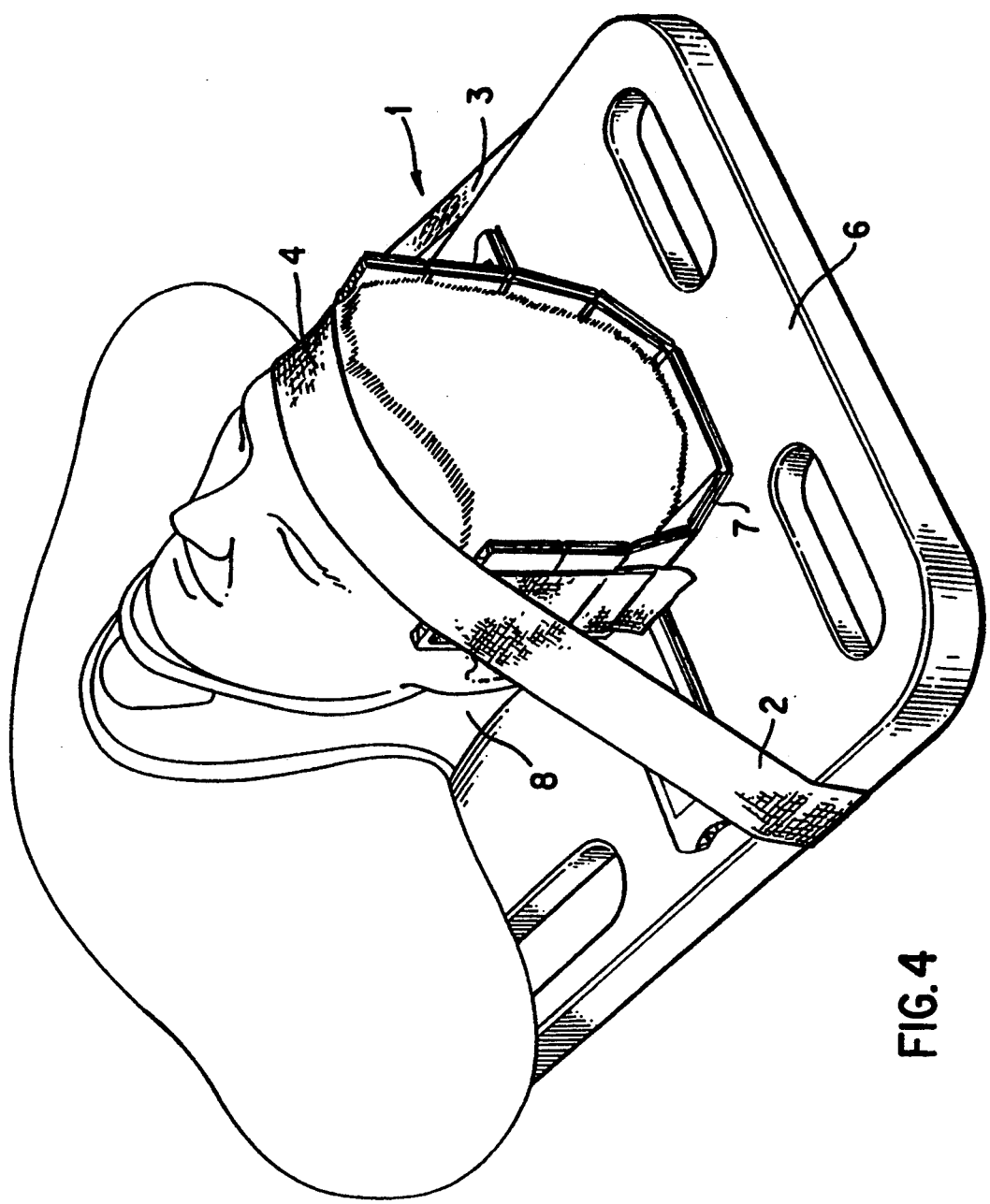
FIG. 4 is a perspective view showing an adhesive strap of the present invention in use.

FIG. 1 shows a preferred embodiment of the adhesive strap of the present invention. The dual adhesive strap 1 has two regions of board contact adhesive 2, 3 on its adhesive side at each of the ends. A region of skin contact adhesive 4 is located on the adhesive side of the strap 1 between the two skin contact adhesive regions 2, 3. The strap 1 and the adhesive regions 2, 3, 4 are preferably large enough to accommodate many sizes of heads, spine boards, and head immobilizers. More preferably, the strap 1 may be approximately 36" long and 2" wide, the board contact adhesive regions 2, 3 each approximately 9" long, and the skin contact adhesive region 4 approximately 18" long.

FIG. 2 is a top view of a preferred embodiment of the present invention showing the markings indicating the different regions and center of the strap 1.

FIG. 3 shows the strap 1, with a removable backing 5, adhered to the board contact regions 2, 3 and the skin contact region 4. To allow quick removal of the backing 5, it may preferably be slightly larger than the strap 1 and/or the board contact regions 2, 3 may not extend to the ends of the strap 1, leaving a portion of the removable backing 5 covering, but not adhered to, the ends of the strap 1.

The dual adhesive strap of the present invention is shown in use in FIG. 4. Once a patient has been placed on a spine board 6 and in a head immobilizer 7, the dual adhesive strap 1 is applied to the patient's forehead and the spine board 6. If the dual adhesive strap 1 has a removable backing 5, it must first be removed to expose the adhesive regions 2, 3, 4. Then the strap may be adhered to the patient's forehead and the spine board 6.

As shown in FIG. 4, the head immobilizer itself may have a strap 9 which lies across the patient's forehead. The dual adhesive strap 1 of the present invention, or at least the skin contact adhesive region 4, can be made wide and sticky enough to cover a substantial portion of the head immobilizer strap 9 and yet adhere to the patient's forehead strongly enough to resist any motion, especially rotation, of the patient's head.

The dual adhesive strap 1 of the present invention is preferably long enough for the board contact adhesive regions 2, 3 to wrap around the side of the spine board 6 and thus adhere to the side and back of the spine board, as shown in FIG. 3. Alternatively, the board contact adhesive regions 2, 3 may not wrap around the spine board 6 but may adhere to only the front of the spine board.

Tables 1-3 summarize the results of tests performed on a preferred embodiment of the dual adhesive strap of the present invention and Johnson & Johnson ZONAS TM adhesive tape. Johnson & Johnson ZONAS TM adhesive tape is the preferred tape of emergency medical personnel for use in conjunction with immobilizing a patient's head. The adhesive used in the skin contact region of the adhesive strap of the present invention was Ecomelt M300, White and the adhesive used in the spine board contact regions was Ecomelt MI-US1000, Turquoise. The Ecomelt M300 adhesive has approximately the same adhesive strength as the Johnson & Johnson ZONAS TM adhesive tape. A much stronger adhesive would not be desirable as the skin contact adhesive, because it could cause injury to the patient's skin. The results shown in Tables 1-3 were obtained using wooden spine boards which constitute approximately 85% of all spine boards currently in use.

Tables 1 and 2 show the results of lap sheer tests performed using the board contact region of the dual adhesive strap of the present invention or Johnson & Johnson ZONAS TM adhesive tape under four different environmental conditions: 1) room temperature and 50% relative humidity.; 2) room temperature and a continuous layer of water; 3) 140° F. and 15% relative humidity; and 4) −20° F. Lap sheer tests were performed by adhering the strap or tape to the top of a wooden spine board, pulling the strap or tape in one direction and the board in the opposite direction, and measuring the pressure, i.e. the lap sheer, at which the adhesive strap or tape became detached from the spine board. The results show that the board contact region of the present invention is consistently more resistant to lap sheer than the Johnson & Johnson ZONAS TM adhesive tape in all the environmental conditions tested.

TABLE 1

| Lap Shear Test of Board Contact Region | | | | |
|---|---|---|---|---|
| Condition | Room Temp. 50% RH* | room temp. continuous water layer | 140° F. 15% RH | −20° F. |
| Lap Shear (PSI) | 44.3 | 41.9 | 6.1 | 103.9 |

*"RH" = relative humidity

TABLE 2

| Lap Shear Test of Johnson & Johnson ZONAS TM Adhesive | | | | |
|---|---|---|---|---|
| Condition | Room Temp. 50% RH* | room temp. continuous water layer | 140° F. 15% RH | −20° F. |
| Lap Shear (PSI) | 39.7 | 30.7 | 5.1 | 31.3 |

Table 3 shows the results of aging tests performed using a head immobilization device like that shown in FIG. 4, containing a head form, attached with the dual adhesive strap of the present invention or Johnson & Johnson ZONAS ™ adhesive tape to a wooden spine board. The strap or tape was adhered to the spine board, the immobilization device and the head form at 150° F. and 80% relative humidity. This apparatus was then allowed to sit for 96 hours in the same environment, and then tested in the same environment. The torque results were obtained by twisting the head form about the axis formed by its neck in either the clock-wise or counter-clockwise direction. The vertical slide results were obtained by moving the head form in the anterior direction, away from the coronal plane and the spine board. The pull load results were obtained by tilting the head form away from the sagittal plane either to the left or to the right.

The results listed in Table 3 are the points where the adhesive strap or tape became detached from the surface it was adhered to or tore the HeadBed II ™. These results show that the dual adhesive strap of the present invention is again more resistant to forces likely to be encountered by a strap for use with a head immobilizer than the Johnson & Johnson ZONAS ™ adhesive tape.

TABLE 3

Aging Test Comparison Results

| | Torque (ft-lbs) | Vertical Slide (ft-lbs) | Pull Load (lbs) |
| --- | --- | --- | --- |
| Pref. Embod. | 80 | 198 | 386.2 |
| ZONAS ™ | 20 | 66.8 | 69.1 |

Although the present invention has been described in terms of particular embodiments and modifications, one of ordinary skill in the art could generate additional embodiments and modifications within the scope of the claimed invention. Accordingly, the description and drawings herein are presented to facilitate an understanding of the present invention, not to limit the scope of the present invention which is claimed below.

What is claimed is:

1. An adhesive strap for immobilizing a patient's head when the head of the patient is placed on a surface, said strap comprising a strap substrate, said substrate comprising a top side and a bottom side, said bottom side comprising a central region comprising skin contact adhesive flanked on each side by a region comprising board contact adhesive, wherein said substrate is of sufficient length so when the central region is in contact with the head of a patient, each of the regions comprising board contact adhesive is of sufficient length to extend beyond said patient's head to contact said surface, and wherein the board contact adhesive is stronger than said skin contact adhesive.

2. The adhesive strap of claim 1, wherein said strap substrate comprises a polyester web.

3. The adhesive strap of claim 1, wherein said top side of said strap substrate comprises markings indicating the location of the center of said strap.

4. The adhesive strap of claim 3, wherein said markings further indicate the location of said adhesive regions.

5. The adhesive strap of claim 1, further comprising a removable backing covering at least said skin contact and board contact adhesive regions.

6. The improved adhesive strap of claim 5, wherein said adhesive strap is precut during the manufacture of said strap.

* * * * *

UNITED STATES PATENT AND TRADEMARK OFFICE
CERTIFICATE OF CORRECTION

PATENT NO. : 5,360,393
DATED : November 1, 1994
INVENTOR(S) : Geoffrey C. Garth, et al It is certified that error appears in the above-indentified patent and that said Letters Patent is hereby corrected as shown below:

Column 6, line 33, Before "adhesive" delete "improved".

Signed and Sealed this

Twenty-fifth Day of April, 1995

Attest:

BRUCE LEHMAN

Attesting Officer     Commissioner of Patents and Trademarks